United States Patent [19]
Mann

[11] Patent Number: 5,575,868
[45] Date of Patent: Nov. 19, 1996

[54] ADHESION TESTING

[76] Inventor: George E. Mann, 1816 Oak St., South Pasadena, Calif. 91030

[21] Appl. No.: 184,429

[22] Filed: Jan. 21, 1994

Related U.S. Application Data

[63] Continuation of Ser. No. 910,625, Jul. 8, 1992, abandoned.

[51] Int. Cl.$^6$ ................................................ B32B 31/00
[52] U.S. Cl. .......................... 156/64; 156/247; 156/344; 156/378; 156/584; 73/150 A
[58] Field of Search ............................ 156/64, 349, 378, 156/584, 344, 358, 247; 73/150 R, 150 A, 788, 842

[56] References Cited

U.S. PATENT DOCUMENTS

| | | | |
|---|---|---|---|
| 3,634,930 | 1/1972 | Cranston | 29/574 |
| 3,745,051 | 7/1973 | Griffin et al. | 161/44 |
| 4,393,699 | 7/1983 | Seiler, Jr. | 73/150 |
| 4,586,371 | 5/1986 | Ivie et al. | 73/150 |
| 4,606,225 | 8/1986 | Thomason et al. | 73/150 |
| 4,822,656 | 4/1989 | Hutter, III | 156/344 X |
| 4,842,912 | 6/1989 | Hutter, III | 156/344 X |
| 4,899,581 | 2/1990 | Allen et al. | 73/150 |
| 5,335,892 | 8/1994 | Busch | 156/344 X |

OTHER PUBLICATIONS

ASTM D 2197–86, Standard Test Method for Adhesion of Organic Coatings by Scrape Adhesion.
ASTM D 3330–76, Standard Test Methods for Peel Adhesion of Pressure–Sensitive Adhesive Tape at 180-Deg Angle.
ASTM D 3359–87, Standard Test Methods for Measuring Adhesion by Tape Test.
ASTM D 4541–85, Standard Method for Pull–Off Strength of Coatings Using Portable Adhesion Testers.
H. Dannenberg, "Measurement of Adhesion by a Blister Method", J. of Applied Polymer Science, vol. V, No. 14, pp. 125–134 (1961).
A. N. Gent and L. H. Lewandowski, "Blow–Off Pressures for Adhering Layers", J. of Applied Polymer Science, vol. 33, pp. 1567–1577 (1987).
A. B. Featherston, Vought Corp., Dallas Texas, "Optimization Of Processing Variables Which Affect Adhesion of Organic Coatings", AD–A048467, Apr. 1977.
William B. Jones, Jr., College of Engineering, University of Utah, Salt Lake City, Utah, "A Simple Test For Certain Cases Of Adhesion", UTEC DO 69–010, Apr. 1969.
J. A. Hinkley, "A Blister Test For Adhesion Of Polymer Films To $SiO_2$", J. Adhesion, 1983, vol. 16, pp. 115–116.

(List continued on next page.)

Primary Examiner—James Sells
Attorney, Agent, or Firm—Charles H. Thomas

[57] ABSTRACT

The present invention provides a method and system for testing the adhesive strength of a bond between a coating or other material, or an adhesive tape, and an underlying surface or substrate to which it is bonded. The test may be performed at room temperature or in an environmental chamber at extreme conditions. In one embodiment an aperture is formed through the substrate and adhesive tape or a coating of paint is applied to the surface surrounding the aperture. A membrane, which approximately maintains its elastic property with only minor yielding during the test, is bonded to the paint or tape, the bond of the membrane to the paint or tape being stronger than the adhesion of the paint, or tape, to the substrate. Pressure is increasingly applied through the aperture, deforming the membrane away from the substrate until the critical pressure is reached and the bond between the paint, or tape, and the substrate fails. The adhesive strength, expressed as the specific work of debonding, is calculated using the critical pressure and a formula based upon constants inherent to the system. In another embodiment the invention may be used for testing the adhesive strength of an adhesive bonding two materials. In yet another embodiment the adhesive strength of a bond between a coating and an underlying surface may be determined in a surface mounted fashion.

18 Claims, 4 Drawing Sheets

OTHER PUBLICATIONS

Mark G. Allen and Stephen D. Senturla, Microasystems Tech. Lab, MIT, Cambridge, MS 02139, "Microfabricated Structures For The Measurement Of Adhesion And Mechanical Properties Of Polymer Films", Proceeding of Amer. Chem. Soc., Div. of Polym. Natl. Science and Eng. 56, pp. 735–739, 1987.

Letter from Terry Say, Director of Research, Rhone–Poulenc, Cranbury, NJ to Dr. Frank Jones, NSF Coating Research Center, Eastern Michigan University, Ypsilanti, MI, including a page of notes of Dr. John Dillard, NSF Center for High Performance Polymeric Adhesives and Composites, Virginia PolyTechnic, Apr. 7, 1992.

ADHESION TESTING

Origin of the Invention

This invention was made with Government support under grant ECD 9119322 awarded by the National Science Foundation. The Government has certain rights in this invention.

CROSS REFERENCE TO RELATED APPLICATION(S)

This is a continuation of U.S. patent application Ser. No. 07/910,625 filed Jul. 8, 1992, now abandoned.

BACKGROUND OF THE INVENTION

1. Field of the Invention

The present invention relates generally to the field of adhesive strength testing and in particular to testing the bonding strength of surface coatings and adhesives.

2. Description of the Prior Art

Three methods are conventionally used to compare or evaluate the adhesive strength of paint or other coatings to an underlying surface or substrate: ASTM D 2197-86, Standard Test Method for Adhesion of Organic Coatings by Scrape Adhesion; ASTM D 3359-87, Standard Test Methods for Measuring Adhesion by Tape Test; and ASTM D 4541-85, Standard Method for Pull-Off Strength of Coatings Using Portable Adhesion Testers. Additionally, there is a conventional method of evaluation for comparing the adhesive strength of adhesive tapes: ASTM D 3330, Test Method for Peel Adhesion of Pressure-Sensitive Tape of 180 Degree Angle.

All of these methods are deficient in that they do not produce an independent standard of measurement for the adhesive strength. For many years those skilled in the art have attempted to find a suitable method for measuring adhesive strength which would provide results independent of the testing process. One such approach is the so-called "blister" method. In this process a fluid, either gas or liquid, is injected under the coating through a hole in its substrate forcing the coating to lift from the substrate in the form of a blister.

A promising enhancement of the blister technique was described by Dannenberg in 1960 (H. Dannenberg, "Measurement of Adhesion by a Blister Method", J. of Applied Polymer Science, Vol. V, No. 14, pp 125–134 (1961)). However, this process is complex and has not been widely accepted.

In 1987 Gent and Lewandowski described a further enhancement of the blister method for the evaluation of the adhesive strength of adhesive tape, but they reported observing several discrepancies in their results. (A. N. Gent and L. H. Lewandowski, "Blow-Off Pressures for Adhering Layers", J of Applied Polymer Science, Vol. 33, pp 1567–1577 (1987)). None of the known blister testing methods have been widely accepted.

One of the principal problems associated with the use of the blister method to evaluate the adhesion of a coating is that the film of the coating will often rupture before the coating debonds from the substrate. Also, the varying elasticities of most coatings will cause varying relationships between the height and the diameter of the paint blister formed, thus producing varying test results. Additionally, to determine bonding strength the blister method requires measuring both the elevation of the paint or other coating from the underlying surface to which it is bonded as well as the pressure at which debonding occurs. This results in a complex calculation. Further, the blister method for testing adhesive tapes used by Gent and Lewandowski has the problem of several unquantifiable variables in the process which lead to inaccurate results.

Another limitation common with conventional blister testing methods is that they must be conducted in a laboratory at normal room temperatures and are not suitable for testing at extreme environmental conditions, such as high or low temperatures.

What is needed is a relatively simple adhesive strength testing method and system which provide consistent measurements of bonding strength, which does not require measuring the elevation before separation, and which can be operated in extreme environmental conditions.

SUMMARY OF THE INVENTION

The preceding and other shortcomings of the prior art are addressed and overcome by the present invention which uses increasing pressure against a membrane bonded to a coating to facilitate the determination of the adhesive strength between a coating and a substrate to which it is bonded by measuring the pressure required to debond the coating from the substrate. The adhesive strength may be determined at room temperatures or at extreme temperatures within an environmental chamber.

In one embodiment, the present invention provides a method of testing adhesive strength by bonding a first surface of a membrane to a coating bonded to a substrate. The bond between the membrane and the substrate has an adhesive strength greater than the adhesive strength of the bond between the coating and the substrate. Increasing pressure is applied to the first surface of the membrane to debond the coating from the substrate. The increasing pressure may be applied to the first surface of the membrane via an aperture through the coating and the substrate or via an aperture in the membrane when a circular groove is made through the coating to the adjacent surface of the substrate.

In a further embodiment, the present invention provides an adhesive strength testing system using a membrane having a first surface bonded to adhesive tape which was first bonded to a substrate. The bond between the membrane and the adhesive tape has an adhesive strength greater than the adhesive strength of the bond between the adhesive tape and the substrate. Increasing pressure is applied to the first surface of the membrane to debond the adhesive tape from the substrate.

In yet another embodiment, the present invention allows for testing the adhesive strength of an adhesive to a substrate. This system uses a membrane having a first surface bonded to a substrate with an adhesive. Increasing pressure is applied through an aperture in the substrate to the first surface of the membrane to debond the membrane from the substrate.

These and other features and advantages of this invention will become further apparent from the detailed description and accompanying figures that follow. In the figures and description, numerals indicate the various features of the invention, like numerals referring to like features throughout both the drawings and the description.

DETAILED DESCRIPTION OF THE PREFERRED EMBODIMENT

The present invention provides a technique for determining the adhesive strength of a bond between selected materials. In a first embodiment the invention provides a means of determining the adhesive strength of a self adhering material or coating applied to a substrate, such as a layer of paint applied to an underlying surface. In another embodiment the invention allows the determination of the adhesive strength of an adhesive tape to a substrate. In yet another embodiment, the invention permits these determinations to be made in a surface mounted fashion, without removing a sample piece of a structure for the underlying substrate. In a further embodiment the invention allows for determining the adhesive strength of an adhesive applied to a substrate.

Figure 1:
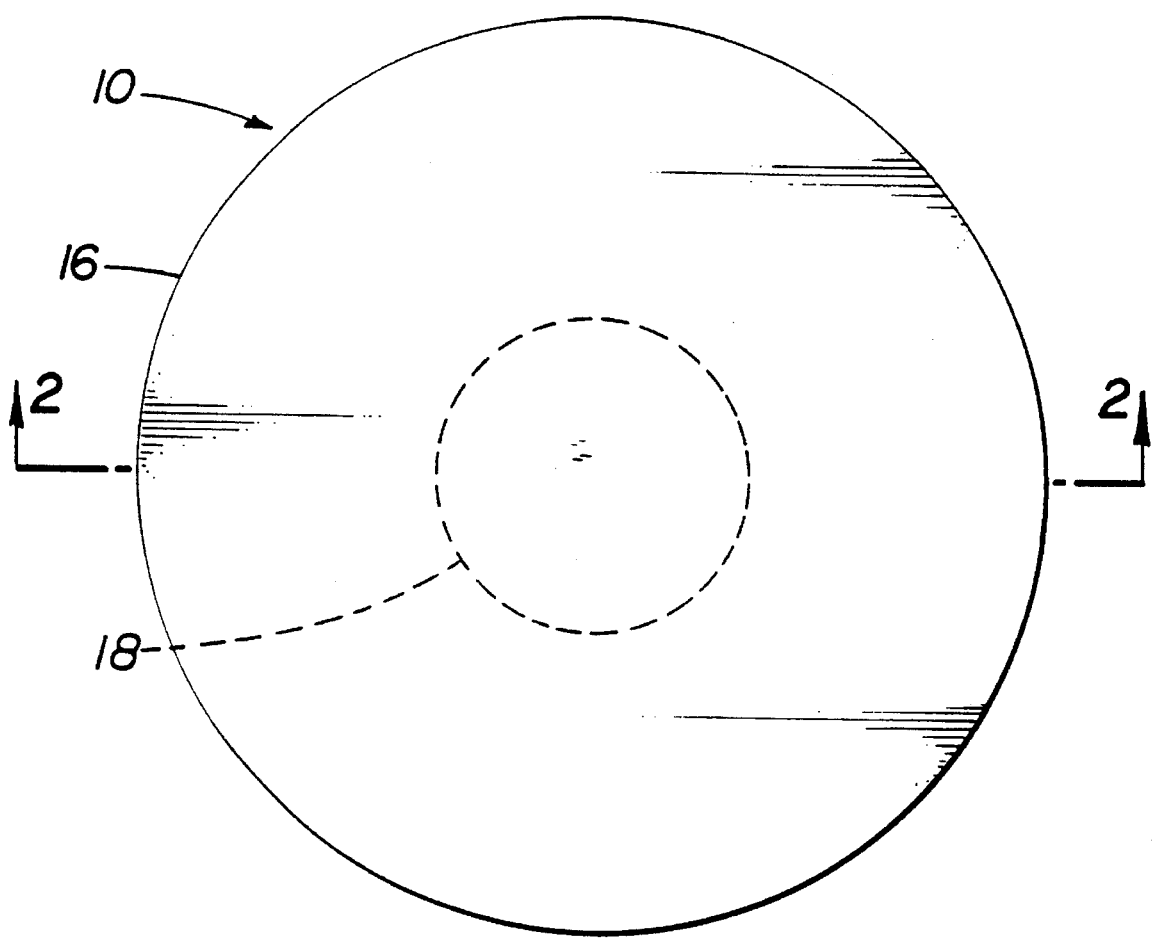
FIG. 1 is a top plan view of an adhesive strength test fixture embodying principles of the current invention.
Figure 2:
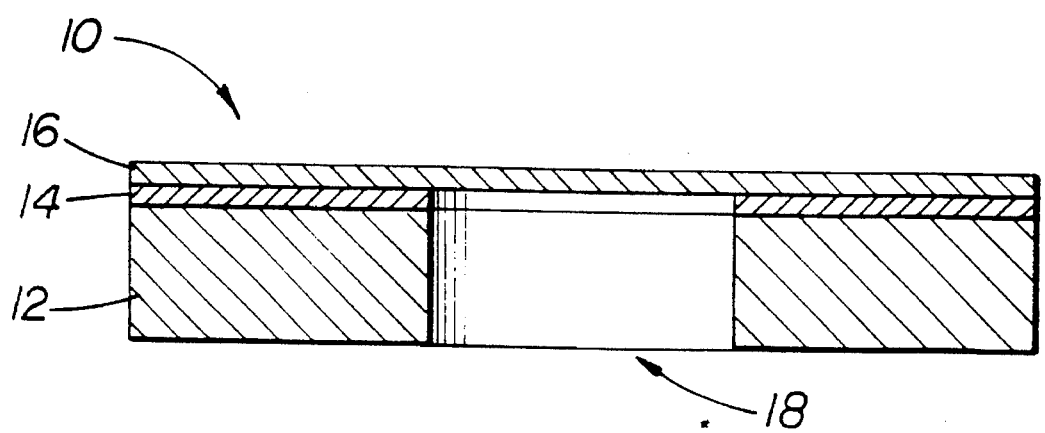
FIG. 2 is a sectional view of the test fixture taken along line 2—2 of FIG. 1.

As generally shown in FIGS. 1 and 2, when used to determine the adhesive strength of a coating such as paint to a substrate, the present invention provides a test fixture 10 having a rigid substrate 12, coating 14, and membrane 16. This invention is used to determine the adhesive strength between substrate 12 and coating 14. If substrate 12 cannot be formed into a rigid, preferably discoid, shaped body, substrate 12 may be bonded to a rigid material such as aluminum (not shown). Membrane 16 is preferably made of a relatively strong material which remains substantially or at least approximately elastic during the test; that is, the membrane can withstand the conditions of the test without greatly exceeding its elastic limit. For example, a thin layer of steel, metal foil or a strong composite material may be used.

Substrate 12 includes aperture 18 which may be formed by drilling through substrate 12. Coating 14 is then applied to a first surface of substrate 12 covering the surface around aperture 18. Alternatively, coating 14 may be applied to the first surface of substrate 12, and substrate 12 then drilled to form aperture 18. Membrane 16 is bonded to coating 14 utilizing an adhesive which results in there being a greater adhesive strength between membrane 16 and coating 14 than between coating 14 and substrate 12. Suitable adhesives include cyanoacrylate and two-part epoxy adhesives.

A fluid, such as an inert gas or liquid, is applied under pressure to the open end of aperture 18 causing the portion of membrane 16 over aperture 18 to deform outward. As membrane 16 deforms, it applies tension to the portion of coating 14 surrounding aperture 18. Fluid pressure is increased until the force applied by membrane 16 exceeds the adhesive strength of coating 14 to substrate 12 causing the portion of coating 14 surrounding aperture 18 to debond from substrate 12.

Figure 3:
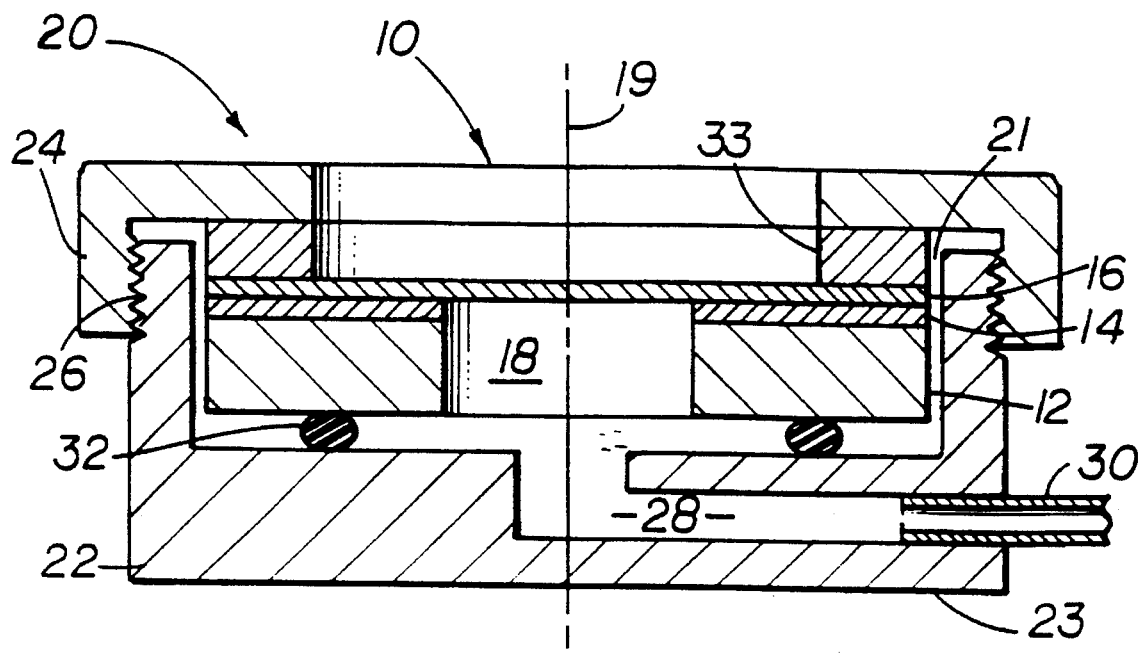
FIG. 3 is a sectional view of a testing test unit embodying principles of the current invention utilizing the test fixture shown in FIGS. 1 and 2.

A suitable system for applying such fluid pressure is shown in FIG. 3. Test unit 20 includes body 22 and retainer 24. Test unit 20 is preferably cylindrical in shape about axis 19, having open end 21 and closed end 23. Retainer 24, shaped like the retainer of a mason jar, is attachable to open end 21 via threads 26.

Body 22 and test fixture 10 are proportioned to permit test fixture 10, like the test fixture shown in FIG. 2, to fit within the interior of body 22. Closed end 23 contains passageway 28 connected to an external source of pressurized fluid via line 30. Passageway 28 is positioned to provide a fluid pathway into aperture 18. The pressurized fluid is prevented from escaping between substrate 12 and closed end 23 by a seal, such as O-ring 32.

Spacer 33, preferably shaped as a ring is positioned between retainer 24 and membrane 16. Tightening retainer 24 onto body 22 causes substrate 12 to compress O-ring 32 thereby creating a fluid tight seal between substrate 12 and closed end 23, as well as between retainer 24, spacer 33 and membrane 16.

The open portions of retainer 24 and spacer 33 are larger than the diameter of aperture 18 and preferably cover only a relatively small portion of membrane 16 adjacent to its perimeter.

Figure 4:
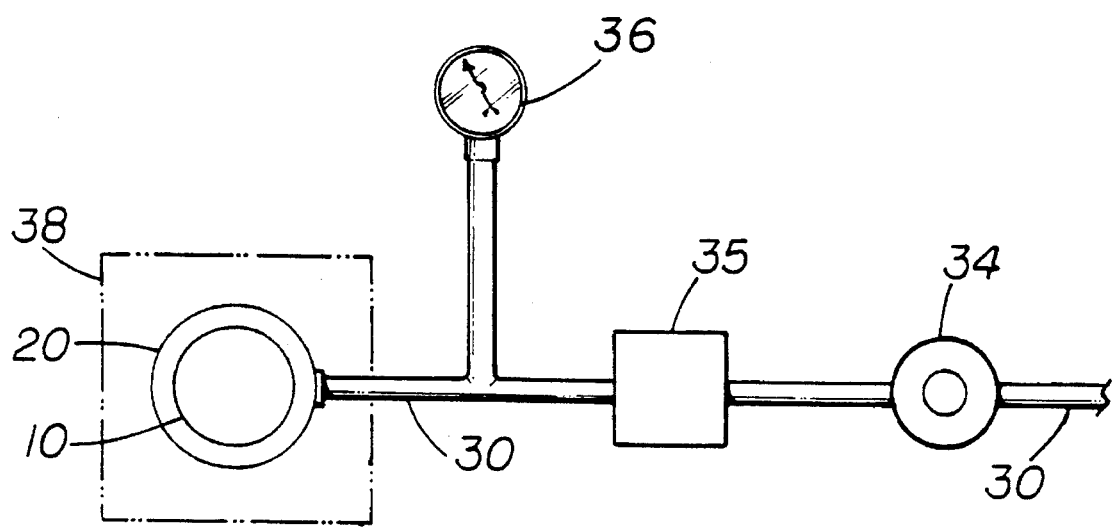
FIG. 4 is a schematic view of a system embodying principles of the current invention.

Referring now to FIG. 4, a schematic of a typical testing system is shown. An external source of fluid (not shown) is provided to line 30. The pressure of the fluid is adjustable by regulator 34. Valve 35 controls the flow of the fluid to test unit 20. Pressure gauge 36 measures the pressure of the fluid within the test system. Pressure gauge 36 may be a mechanical or digital device, preferably with the capability of recording pressure measurements and/or indicating scale pressure.

In operation, test fixture 10 is enclosed within test unit 20 as described above. Pressurized fluid is supplied to test fixture 10 and pressure is increased until coating 14 debonds from substrate 16. The pressure at the moment of debonding is recorded as the critical pressure.

The measurement of the adhesive strength by the system is calculated as a function of the system design and the critical pressure. The following formula is used to determine the bonding strength:

$$\text{Specific work of debonding, } G = m\, P^n,$$

where "P" is the critical pressure and "m" and "n" are constants inherent to the system design. After system check is completed, it is necessary only to observe the critical pressure. Critical pressure may be directly translated on pressure gauge 36, and the specific work of debonding may be determined in any system of units (e.g., English, metric or SI) using a digital system.

Test unit 20 may be placed in chamber 38 during testing to determine the effects of environmental conditions, such as extreme temperatures or corrosive atmospheres, upon the adhesive strength of a material. To further evaluate the effects of a corrosive environment upon adhesive strength, a corrosive gas or liquid may be used as the pressurizing fluid.

A further embodiment for testing the adhesion of a coating to a substrate is described in greater detail below with regard to FIG. 8.

Figure 5:
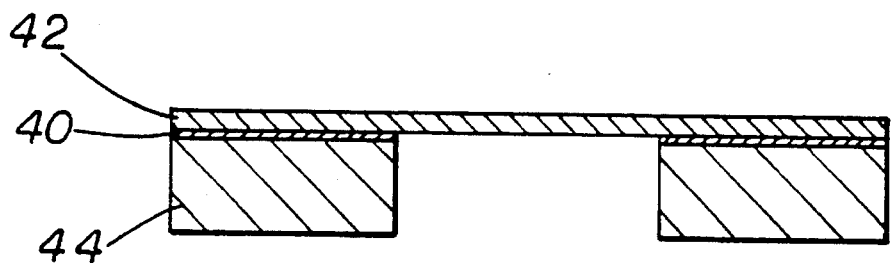
FIG. 5 is a sectional view of a test fixture used to test the adhesive strength of an adhesive.

In addition to determining the adhesive strength of a coating to a substrate, the invention may be used to evaluate the bonding strength of an adhesive to various materials. Referring to FIG. 5, adhesive 40 is applied directly between two selected materials formed as membrane 42 and substrate 44. The resulting structure is tested as described above.

Figure 6:
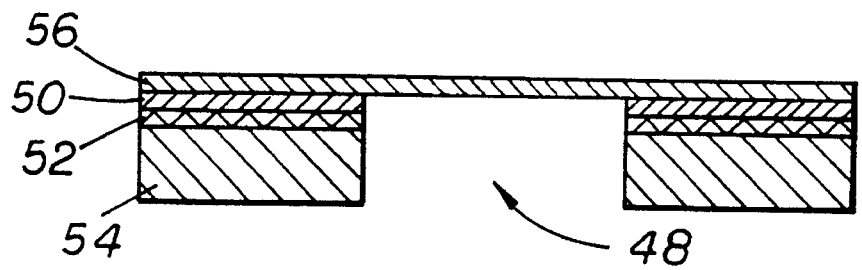
FIG. 6 is a sectional view of a test fixture used to test the adhesive strength of an adhesive with selected materials.

If the selected materials are not sufficiently elastic and rigid for use as membrane 42 and substrate 44, respectively, the following structure is used. Referring to FIG. 6, selected materials 50 and 52 are formed into flat rings and bonded together with the adhesive to be tested. Selected material 52 is bonded to rigid substrate 54, into which aperture 48 has been formed equal in size to the openings in selected materials 50 and 52. Rigid substrate 54 may be made of aluminum or other similarly rigid material. Membrane 56, which may be made of steel or other strong metallic foil, is bonded to selected material 50 completing the structure. The bond between membrane 56 and selected material 50 and the bond between substrate 54 and selected material 52 are formed to be stronger than the bonding strength of the adhesive to be tested. This structure is then tested as described above.

The invention may additionally be used to evaluate the adhesive strength of adhesive tape. In this embodiment, adhesive tape is substituted for coating 14 in FIG. 3. Still referring to FIG. 3, when testing adhesive tape, the adhesive side of the adhesive tape is attached to substrate 12, and membrane 16 is bonded to the nonadhesive side of the tape. A further embodiment for testing the adhesive strength of adhesive tape is discussed in more detail below with regard to FIG. 10.

Figure 7:
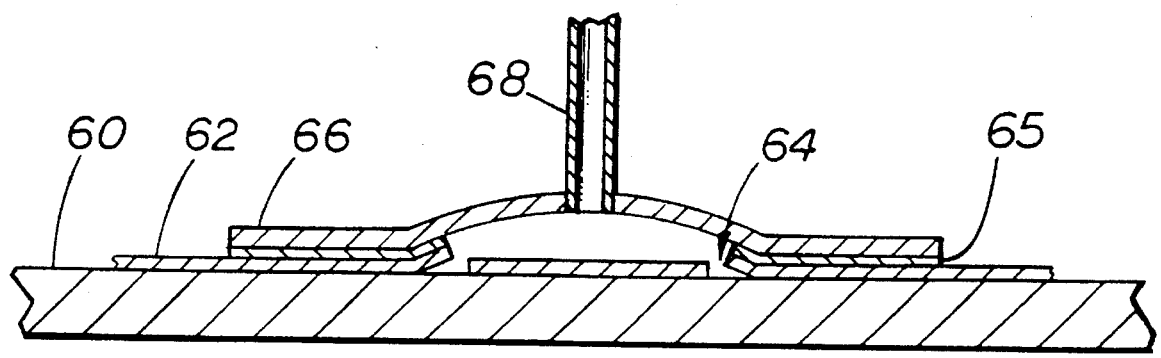
FIG. 7 is a sectional view of another embodiment of the current invention permitting surface mounted adhesive strength testing.

In another embodiment the invention may be used in a surface mounted fashion to test the adhesive strength of paint and other coatings to surfaces where it is neither practical to form an aperture through the surface nor practical to remove a sample portion of the underlying surface. Referring to FIG. 7, surface 60 is coated with paint layer 62. To test the bonding strength of paint layer 62 to surface 60 circular groove 64 is cut through paint layer 62 without damaging surface 60.

Membrane 66 is placed over paint layer 62 covering the area of paint layer 62 inside groove 64, and covering a portion of paint layer 62 outside groove 64, enclosing the entire perimeter of groove 64. The portion of membrane covering paint layer 62 outside groove 64 is bonded to the corresponding portion of paint layer 62 with adhesive 65 which results in there being a greater adhesive strength between membrane 66 and paint layer 62 than between paint layer 62 and surface 60. Membrane 66 is preferably circular in shape, having tube 68 fixed at or near an aperture in its center permitting the space between membrane 66 and paint layer 62 to be filled with a fluid and pressurized.

A testing system similar to that described above and shown in FIG. 4, is connected to tube 68, and the pressure is increased until the critical pressure is reached. The adhesive strength may then be determined as previously described. FIG. 7 depicts this embodiment of the invention just after completion of a test, showing the failure of the bond between paint layer 62 and surface 60.

Figure 8:
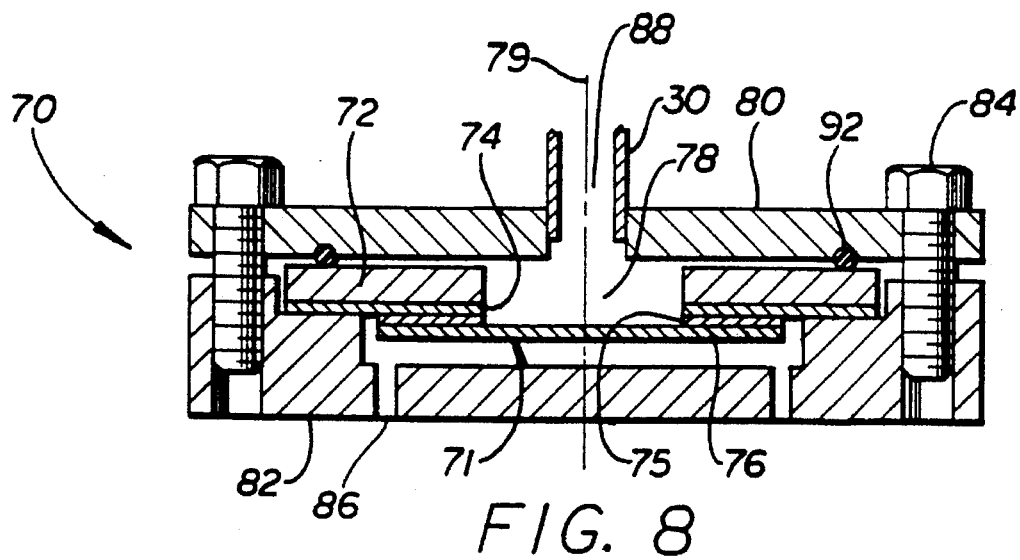
FIG. 8 is a sectional view of a test unit used to determine the adhesive strength of a coating to a substrate.

In a further embodiment of an adhesion tester FIG. 8 shows test unit 70 for testing the adhesion strength of a coating to a substrate. Test unit 70 contains test fixture 71. Test fixture 71 includes substrate 72 covered with coating 74 with membrane 76 bonded thereto.

Substrate 72 is circular and contains aperture 78. Coating 74 may be applied to a first side of substrate 72 after aperture 78 has been created in substrate 72. More specifically, aperture 78 may be cut or drilled in substrate 72, and then a cork or similar stopping means (not shown) may be placed in aperture 78 and coating 74 applied. Alternatively, aperture 78 may be cut or drilled in substrate 72 after coating 74 has been applied to a first side of substrate 72. With any of these methods, substrate 72 with coating 74 bonded to its first side and having aperture 78 therethrough results.

Membrane 76 is then bonded over aperture 78 to coating 74 with adhesive 75. Suitable substances for adhesive 75 include cyanoacrylate and two-part epoxy adhesives. There is a greater adhesive strength between membrane 76 and coating 74 than between coating 74 and substrate 72. Membrane 76 is circular and has a smaller diameter than substrate 72. Further, membrane 76 does not contain an aperture, and membrane 76 must have a diameter greater than the diameter of aperture 78 of substrate 72. Additionally, the diameter of membrane 76 is preferably smaller than the diameter of substrate 72 so that it does not interfere with the seal between test unit 70 and coating 74 covered substrate 72 described below. Test fixture 71 is then positioned within test unit 70.

Test unit 70 includes base 82 in which substrate 72 rests. In positioning test fixture 71 in test unit 70, the side of substrate 72 covered with coating 74 is placed onto base 82. This placement is upside down of the placement depicted in FIG. 3. Referring again to FIG. 8, base 82 is formed so that membrane 76 does not touch base 82 when test fixture 71 is positioned in test unit 70. Cover 80 is then placed on top of test fixture 71, enclosing test fixture 71 within test unit 70. Cover 80 is fastened to base 82 by fastener 84, a screw or similar means for fastening, forming a fluid tight seal with substrate 72 by use of a seal such as O-ring 92 placed between cover 80 and substrate 72. Cover 80 includes cover aperture 88 to which line 30 is attached. This device is then used to test the adhesive strength of coating 74 to substrate 72.

To determine the adhesive strength of coating 74 to substrate 72, a system like that described in FIG. 4 is used to apply a pressurized fluid to test fixture 71 through line 30 along axis 79 through aperture 78. In this way, pressure is applied against membrane 76 until coating 74 debonds from substrate 72.

Test unit 70 further includes passage way 86 in base 82 which allows for air and pressurized fluid to escape from test unit 70 when membrane 76 and coating 74 elevate from substrate 72. Passage way 86 was created to eliminate resistance against the side of membrane 76 not bonded to coating 74 resulting from a pocket of air between test fixture 71 and base 82 thus eliminating any affect on the measurements. Test unit 70 may be substituted for test unit 20 in FIG. 4 so the critical pressure may be measured and so testing may be achieved under various conditions.

Figure 9:
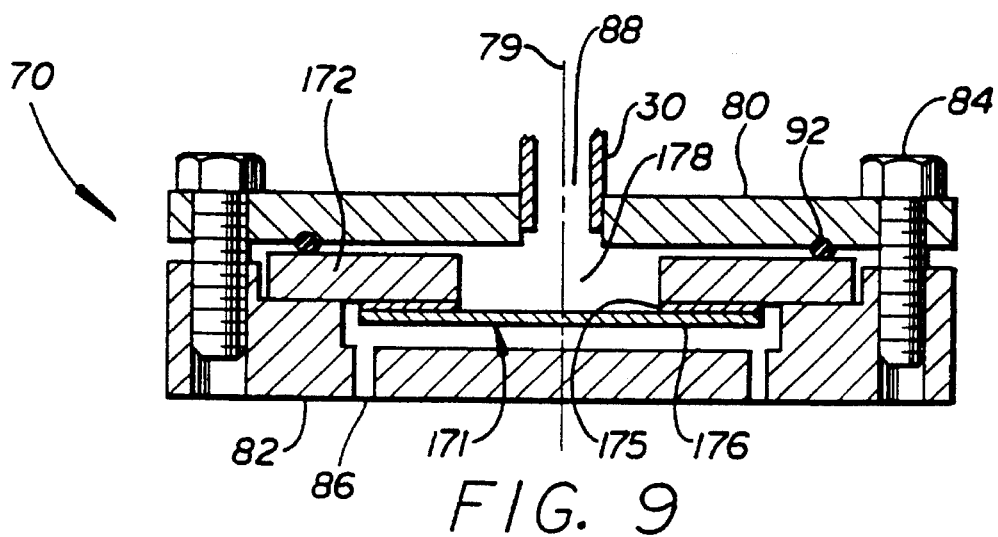
FIG. 9 is a sectional view of a test unit used to determine the adhesive strength of an adhesive to a substrate.
Figure 10:
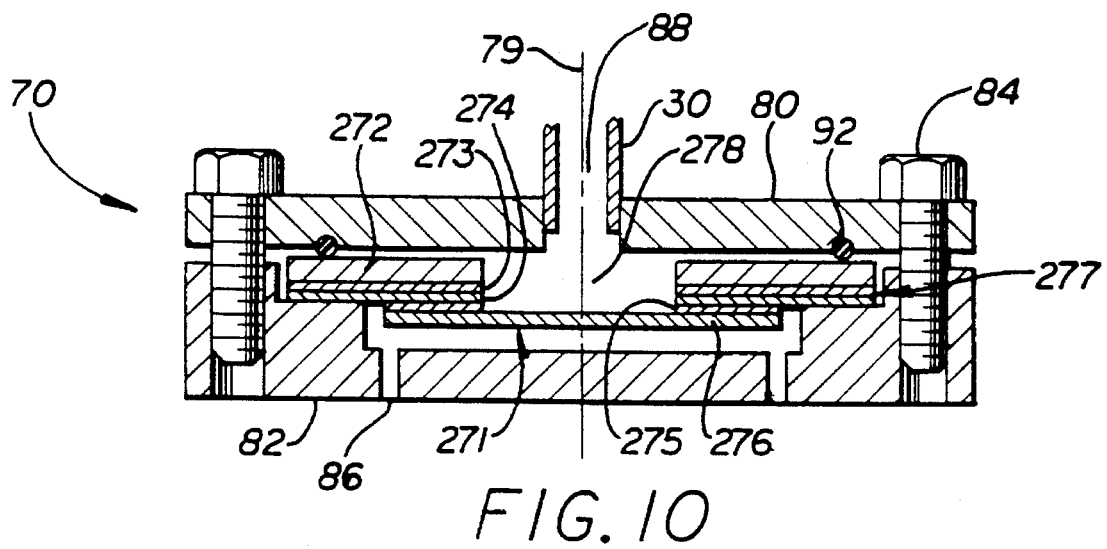
FIG. 10 is a sectional view of a test unit used to determine the adhesive strength of adhesive tape to a substrate.

Test unit 70 may also contain test fixtures allowing for testing the adhesive strength of an adhesive to a substrate, as shown in FIG. 9, and of an adhesive tape to a substrate, as shown in FIG. 10.

In another embodiment of an adhesion tester FIG. 9 depicts adhesion test unit 70 for determining the adhesive strength of adhesive 175 to substrate 172. Test unit 70 contains test fixture 171. Test fixture 171 includes substrate 172 in which aperture 178 is cut or drilled. Adhesive 175 is applied to substrate 172, and then membrane 176 is bonded to substrate 172, covering aperture 78.

Test fixture 171 is then positioned inside test unit 70 as described above. A system like that described in FIG. 4 is then used to apply a pressurized fluid through line 30 to test fixture 171 along axis 79 through aperture 178. In this way pressure is applied against membrane 176 until adhesive 175 fails and membrane 176 debonds from substrate 172. As discussed above, test unit 70 may be substituted for test unit 20 in FIG. 4 for measuring the critical pressure and testing test fixture 171 under various conditions.

In yet another embodiment of an adhesion tester FIG. 10 depicts adhesion test unit 70 for determining the adhesive strength of adhesive tape 277 to substrate 272. Test unit 70 contains test fixture 271 which includes substrate 272 to which adhesive tape 277 is attached. After adhesive tape 277 is attached to substrate 272 with adhesive tape adhesive layer 273, aperture 278 is cut or drilled in both substrate 272 and attached adhesive tape 277. Alternatively, aperture 278 may be cut or drilled in substrate 272 and then adhesive tape 277 with like sized aperture attached. With either method substrate 272 with adhesive tape 277 bonded thereto, having aperture 278 results.

Membrane 276 is then bonded to adhesive tape backing layer 274 with adhesive 275. Then test fixture 271 is positioned inside test unit 70 as described above, and a system like that described in FIG. 4 is used to apply a pressurized fluid through line 20 to test fixture 271 along axis 79 through aperture 278. In this way pressure is applied against membrane 276 until adhesive tape 277 debonds from substrate 272. As discussed above, test unit 70 may be substituted for test unit 20 in FIG. 4 for measuring the critical pressure and for testing test fixture 271 under various conditions.

Having now described the invention in accordance with the requirements of the patent statutes, those skilled in this art will have no difficulties making changes and modifications in the embodiment of the individual elements of the invention in order to meet their specific requirements or conditions. Such changes and modifications may be made without departing from the scope and spirit of the invention as set forth in the following claims.

What is claimed is:

1. A method for testing the adhesive strength of a testing article bonded to a substrate, the method comprising the steps of:

bonding a first surface of a membrane to the testing article, the adhesive strength of the bond between the membrane and the testing article being greater than the adhesive strength of the bond between the testing article and the substrate; and determining the critical pressure required to substantially debond a continuous periphery of an aperture in the testing article from the substrate, the critical pressure being directly related to the specific work of adhesion.

2. The method of claim 1 wherein the step of determining the critical pressure further comprises the step of:

determining the adhesive strength of the bond between the testing article and the substrate as a function of the specific work of substantially debonding the testing article from the substrate.

3. The method of claim 1 wherein the step of determining the critical pressure further comprises:

measuring the pressure at the moment the bond between the testing article and the substrate fails.

4. The method of claim 1 further comprising the step of:

providing a membrane that remains approximately elastic when subjected to the pressure applied to debond the testing article from the substrate.

5. The method of claim 1 further comprising the step of:

bonding a coating to the substrate.

6. The method of claim 1 wherein the step of bonding a first surface of a membrane to the testing article further comprises the step of:

bonding the membrane to a portion of the testing article surrounding an aperture therethrough; and wherein the step of applying increasing pressure further comprises:

applying increasing pressure through an aperture in the membrane.

7. The method of claim 1 wherein the step of determining the critical pressure further comprises:

applying increasing pressure through apertures in the substrate and the testing article.

8. The method of claim 7 wherein the step of applying increasing pressure further comprises:

applying pressurized fluid.

9. The method of claim 7 wherein the step of bonding a first surface of a membrane further comprises:

using the membrane to seal the apertures in the substrate and the testing article.

10. A system for testing the adhesive strength of a testing article bonded to a substrate, comprising:

a membrane with a first side bonded to the testing article, the adhesive strength of the bond between the membrane and the testing article being greater than the adhesive strength of the bond between the testing article and the substrate;

means for applying increasing pressure to debond the testing article from the substrate; and means for determining the critical pressure required to substantially debond a contiguous periphery of an aperture in the testing article from the substrate, said critical pressure being directly related to the specific work of adhesion.

11. The system of claim 10 wherein the means for determining the critical pressure further comprises:

means for determining the adhesive strength of the bond between the testing article and the substrate directly from the pressure required to cause bond substantial failure as a function of the specific work of debonding the testing article from the substrate.

12. The system of claim 10 wherein the means for determining the critical pressure further comprises:

means for measuring the pressure at the moment the bond between the testing article and the substrate fails.

13. The system of claim 10 in which the membrane remains approximately elastic when subjected to the pressure applied to debond the testing article from the substrate.

14. The system of claim 10 wherein the testing article is a coating bonded to the substrate.

15. The system of claim 10 wherein the membrane is bonded to a portion of the testing article surrounding an aperture therethrough, wherein the means for determining the critical pressure further comprises:

means for applying increasing pressure through an aperture in the membrane.

16. The system of claim 10 wherein the means for determining the critical pressure further comprises:

means for applying increasing pressure through apertures in the substrate and the testing article.

17. The system of claim 16 wherein the means for determining the critical pressure further comprises:

pressurized fluid.

18. The system of claim 16 wherein the membrane seals the apertures in the substrate and testing article.

* * * * *